(12) United States Patent
Cai et al.

(10) Patent No.: US 9,492,590 B2
(45) Date of Patent: Nov. 15, 2016

(54) BIOMATERIAL

(75) Inventors: Qian Cai, Hertfordshire (GB); Mervyn Little, Hertfordshire (GB); Thomas Buckland, Hertfordshire (GB)

(73) Assignee: ApaTech Limited, Elstree, Hertfordshire (GB)

( * ) Notice: Subject to any disclaimer, the term of this patent is extended or adjusted under 35 U.S.C. 154(b) by 1021 days.

(21) Appl. No.: 13/640,717

(22) PCT Filed: Apr. 18, 2011

(86) PCT No.: PCT/GB2011/000599
§ 371 (c)(1),
(2), (4) Date: Feb. 27, 2013

(87) PCT Pub. No.: WO2011/128655
PCT Pub. Date: Oct. 20, 2011

(65) Prior Publication Data
US 2013/0145963 A1    Jun. 13, 2013

Related U.S. Application Data

(60) Provisional application No. 61/387,763, filed on Sep. 29, 2010.

(30) Foreign Application Priority Data

Apr. 16, 2010 (GB) .................... 1006422.8
Aug. 24, 2010 (GB) .................... 1014136.4

(51) Int. Cl.
*A61L 27/44* (2006.01)
*A61L 24/00* (2006.01)

(52) U.S. Cl.
CPC ............ *A61L 27/44* (2013.01); *A61L 24/0073* (2013.01)

(58) Field of Classification Search
None
See application file for complete search history.

(56) References Cited

U.S. PATENT DOCUMENTS

| | | |
|---|---|---|
| 5,470,803 A | 11/1995 | Bonfield et al. |
| 5,641,502 A | 6/1997 | Skalla et al. |
| 6,187,047 B1 | 2/2001 | Kwan et al. |
| 6,292,667 B1 | 9/2001 | Wallentin et al. |
| 6,312,468 B1 | 11/2001 | Best et al. |
| 6,527,810 B2 | 3/2003 | Johnson et al. |
| 6,582,672 B1 | 6/2003 | Bonfield et al. |
| 6,585,946 B1 | 7/2003 | Bonfield et al. |
| 7,241,813 B2 | 7/2007 | Kay et al. |
| 7,282,216 B2 | 10/2007 | Costantino et al. |

(Continued)

FOREIGN PATENT DOCUMENTS

| | | |
|---|---|---|
| JP | 2006-521425 A | 9/2006 |
| WO | WO2004071451 A2 | 8/2004 |

(Continued)

*Primary Examiner* — Melvin C Mayes
*Assistant Examiner* — Stefanie Cohen
(74) *Attorney, Agent, or Firm* — Bret E. Field; Bozicevic, Field & Francis LLP

(57) ABSTRACT

A biocompatible material comprising a resorbable polymer matrix and at least one additive, wherein the resorbable polymer matrix comprises: (i) at least one non-random copolymer of poly (alkylene oxide) s, and (ii) at least one poly (alkylene glycol) polymer and/or at least one methoxy-poly (alkylene glycol) polymer, and wherein the at least one additive is selected from solid particles, porous particles, hollow particles, polymers, inert fillers, bioactive compounds, color pigments and combinations of two or more thereof.

15 Claims, 7 Drawing Sheets

(56) References Cited

U.S. PATENT DOCUMENTS

| | | |
|---|---|---|
| 7,534,451 B2 | 5/2009 | Erbe et al. |
| 7,538,162 B2 | 5/2009 | Haider et al. |
| 7,553,913 B2 | 6/2009 | Wellisz et al. |
| 7,799,839 B2 | 9/2010 | Yun et al. |
| 7,829,616 B2 | 11/2010 | Wellisz et al. |
| 7,842,300 B2 | 11/2010 | Atkinson et al. |
| 7,875,342 B2 | 1/2011 | Smith et al. |
| 8,124,687 B2 | 2/2012 | Wellisz et al. |
| 8,153,148 B2 | 4/2012 | Maspero et al. |
| 8,439,930 B2 | 5/2013 | Campion et al. |
| 2002/0127196 A1 | 9/2002 | Avila et al. |
| 2003/0095945 A1* | 5/2003 | Levy ............. A61L 24/04 424/78.38 |
| 2005/0171328 A1* | 8/2005 | Harris ........... A61K 47/48215 528/322 |
| 2006/0140904 A1 | 6/2006 | Wellisz et al. |
| 2007/0015834 A1 | 1/2007 | Flashner-Barak et al. |
| 2009/0286886 A1* | 11/2009 | Fisher ............. A61L 24/0042 514/772.3 |
| 2009/0306789 A1 | 12/2009 | Buckland et al. |
| 2010/0262258 A1 | 10/2010 | Gibson et al. |
| 2010/0322867 A1 | 12/2010 | Gibson et al. |
| 2010/0324500 A1 | 12/2010 | Buckland et al. |
| 2011/0054615 A1 | 3/2011 | Buckland et al. |
| 2011/0059151 A1 | 3/2011 | Buckland et al. |

FOREIGN PATENT DOCUMENTS

| | | | |
|---|---|---|---|
| WO | WO2004071452 A2 | 8/2004 | |
| WO | WO 2007139760 A2 * | 12/2007 | ......... A61L 24/0042 |
| WO | WO 2011/009635 A1 | 1/2011 | |

* cited by examiner

BIOMATERIAL

The present invention relates to biocompatible materials and, in particular, to polymer matrices for use in biomedical applications.

In the fields of medicine, surgery, and dentistry, it is common to use a particulate implantable material to serve as a framework for tissue in-growth. There are various sources for the particulate component, both natural and synthetic implantable substances. They include, but are not limited to, native autogenous bone or cartilage, allogeneous bone or cartilage, collagen, hydroxyapatite, Si-substituted hydroxyapatite, β-tricalcium phosphate, polymethylmethacrylate (PMMA), polytetrafluoroethylene (PTFE), polyethylene, and dimethylpolysiloxane. Due to their particulate nature, these materials are often not easy to use, and practitioners will often mix the materials with some aqueous medium to facilitate their application, which will inevitably increase the preparation time. An alternative is to add the particulate implants into a matrix to temporarily adhere them to one another. The particulate components with the matrix therefore form a putty- or paste-like substance with markedly improved handling properties. Furthermore, it is desirable that these putty- or paste-like substances have a customizable adhesiveness, which will allow them to stay or stick onto the surface or defect sites during and after the surgical procedure.

The requirements of non-toxic and biocompatible matrices with handling characteristics ranging from oil-like to wax-like properties in the medical, dental and surgical fields have never been met. Desirable materials forming the matrix should ideally possess the following properties: low or no toxicity; biocompatibility; stability during storage; biodegradability under physiological conditions within a certain period of time; simple and inexpensive to manufacture and store; and variable packability or malleability.

Matrices currently used include hydrogels (US 2010/0034883 A1), biodegradable polyesters (U.S. Pat. No. 6,322,797 B1) and petroleum-based hydrocarbon compounds (U.S. Pat. No. 6,461,420 B2). Hydrogels lack the appropriate handling characteristics in that they lack plasticity, and are often unstable when compressive forces are applied to them. Biodegradable polyesters will inevitably generate acidic degradation by-products, which are not favourable for bone implantation, due to their chemical nature of synthesis. Petroleum-based hydrocarbon compounds are hydrophobic, insoluble in water or other aqueous media, and chemically inert. As a consequence, they cannot be dissolved, resorbed, metabolized or otherwise removed by the body.

A number of synthetic bone graft substitutes currently on the market, which incorporate carrier materials, do not have the ability to remain in place and are prone to fall apart when subject to external forces. In addition, these known materials are often too stiff and, therefore, when applied onto the substrate surface, tend to leave gaps between the interfaces. Such gaps are detrimental to bone integration and healing.

Accordingly, it is an object to provide a biocompatible material for use in biomedical applications which overcomes at least some of the problems associated with the prior art. Another object is to provide a biocompatible material which provides a commercially acceptable alternative to materials known in the art.

In a first aspect there is provided a biocompatible material comprising a resorbable polymer matrix and at least one additive,
wherein the resorbable polymer matrix comprises:
(i) at least one non-random copolymer of poly(alkylene oxide)s, and
(ii) at least one poly(alkylene glycol) polymer and/or at least one methoxypoly(alkylene glycol) polymer,
and wherein the at least one additive is selected from solid particles, porous particles, hollow particles, polymers, inert fillers, bioactive compounds, colour pigments and combinations of any two or more thereof.

Definitions of a number of terms used throughout the specification are provided below.

The term "biocompatible material" used herein refers to a material that does not threaten, impede, or adversely affect living tissue.

The term "resorbable polymer matrix" used herein means a polymer composition which can be broken down and assimilated back into the body.

The term "copolymer" used herein (also known as a heteropolymer) refers to a polymer derived from two or more types of monomeric species. This is in contrast to a homopolymer where only one type of monomer is used.

The term "non-random" used herein means that the intrachain distribution of co-monomers has a particular pattern and is segmented. It is a unique structural feature of a block copolymer.

The term "poloxamer" used herein refers to a nonionic triblock copolymer composed of a central hydrophobic chain of polyoxypropylene (poly(propylene oxide)) flanked by two hydrophilic chains of polyoxyethylene (poly(ethylene oxide)).

The term "poloxamine" used herein refers to a polyoxyethylene-polyoxypropylene (POE-POP) block copolymer where a POE-POP unit is linked to another POE-POP unit by ethylenediamine and having the general structure $(POE_n\text{-}POP_m)_2\text{—N—}C_2H_4\text{—N—}(POP_m\text{—}POE_n)_2$.

The term "weight average molecular weight" used herein is calculated as follows:

$$M_w = \frac{\sum_i N_i M_i^2}{\sum_i N_i M_i}$$

where $N_i$ is the number of molecules of molecular weight $M_i$.

Each aspect or embodiment described herein may be combined with any other aspect(s) or embodiment(s) unless clearly indicated to the contrary. In particular any feature indicated as being preferred or advantageous may be combined with any other feature or features indicated as being preferred or advantageous.

The biocompatible material described herein is suitable for use in therapy. Such therapy includes, but is not restricted to, medicine, dentistry and surgery. More specific applications include the use as a surgical adhesive, a hemostatic agent, a surgical lubricant, an excipient for implantation, or a cohesive matrix to hold small objects (for example bone fragments and/or particulate materials) in place at a site of surgery.

The biocompatible materials are suitable as bone grafts, bone fillers and bone scaffolds. The materials are particularly suitable for use as synthetic bone graft substitutes. In this case, the resorbable polymer matrix acts as a carrier for loose granules such as, for example, bone filler granules and/or powders.

In a preferred embodiment, the biocompatible material is capable of adhering to one or more of bone, tooth, skin, mucous membranes and other body tissue.

In the biocompatible material the resorbable polymer matrix will typically comprise the continuous phase and the at least one additive will typically comprise the non-continuous, dispersed phase.

Known materials, such as petroleum-based hydrocarbon compounds, when introduced to tissues, remain at the site of application indefinitely. Over time, the wax or grease will cause inflammation and interfere with healing. For example, beeswax can remain as a foreign body for many years, causing a giant cell reaction and local inflammation at the site of application. Moreover, beeswax inhibits osteogenesis, which is critical for bone healing, even in very small amounts. Therefore, beeswax should not be used where bone healing or fusion is required. In contrast, the resorbable polymer matrix described herein is preferably biocompatible and non-toxic to living tissues. Under physiological conditions, the resorbable polymer composition is resorbable from the body without remaining a barrier to compromise wound healing or persist as a foreign body. In particular, the dissolved polymer is not metabolized, but eliminated from the body by renal excretion in an unmodified form.

The more the material and/or resorbable polymer matrix is worked (for example, moulding by a surgeon prior to implantation), the softer and tackier it becomes. This can lead to problems with handling. For example, the material may adhere to a surgeon's gloves. However, by controlling the identities and weight percents of the components of the matrix used in the first aspect, tackiness can be reduced. In particular, by decreasing the ratio of oxyethylene groups in the copolymer structure it has been shown experimentally that the composition becomes stiffer and less tacky. The stiffness of the composition can be compensated for by the addition of poly (ethylene glycol) or methoxypoly (ethylene glycol). Advantageously, the materials exhibit reduced tackiness while retaining adequate surface adhesiveness to a defect site enabling the material to remain in place without granule shedding. As a result, the working window can be expanded and optimised.

The at least one non-random copolymer of poly(alkylene oxide)s includes derivatives thereof. The at least one poly (alkylene glycol) polymer and/or at least one methoxypoly (alkylene glycol) polymer includes derivatives thereof.

The at least one non-random copolymer of poly(alkylene oxide)s can be linear or branched.

In a preferred embodiment, the at least one non-random copolymer of poly(alkylene oxide)s has a weight average molecular weight of less than or equal to 40,000 g/mol. Non-random copolymers of poly(alkylene oxide)s with weight average molecular weight greater than 40,000 g/mol cannot be readily removed from the body without metabolism, which may lead to problems of toxicity. In particular, such copolymers cannot be easily dissipated through the renal system and cause inflammation or foreign body reactions. It is also advantageous if the at least one non-random copolymer of poly(alkylene oxide)s has a weight average molecular weight of at least 2000 g/mol. Copolymers with a weight average molecular weight of at least 2000 g/mol result in improved mouldability and retention properties.

In an alternative embodiment, the at least one non-random copolymer of poly(alkylene oxide)s can have a weight average molecular weight in the range of from 200 g/mol to 1000 g/mol, from 1000 g/mol to 4000 g/mol, from 4000 to 8000 g/mol, or from 8000 g/mol to 20,000 g/mol. Controlling the weight average molecular weight of the poly(alkylene oxide) results in improvement of the material's handling properties, such as a lower deformation force, and a longer working window.

Existing products can only achieve one of either the ability to wick blood or the ability to facilitate clotting. This often results in the need for blood suction, compression and the application of gauze to absorb pools of shed blood, or distortion of the defect site to facilitate the localisation of bone graft substitutes, the nutrition supply and the resultant blood vascularisation and new bone growth integration with the healthy surrounding bone structure.

In a preferred embodiment, the at least one non-random copolymer of poly(alkylene oxide)s comprises a poloxamer or poloxamine. The use of poloxamers and/or poloxamines has been found to render the matrix better able to wick blood and facilitate clotting. This results from the poloxamer/poloxamine structure. Part of the poloxamer/poloxamine structure is hydrophilic and, therefore, combined with the wicking-properties of the at least one additive (for example ceramic granules), the composition will readily absorb and suck the surrounding blood into or around the grafting material. On the other hand, another part of the poloxamer/poloxamine structure is hydrophobic and can behave as tamponading plugs to the holes and spaces in the bone to stop bleeding. The presence of poloxamer/poloxamine and the at least one additive can result in a synergic effect with regard to improving blood wicking and clotting at the local defect site.

In a preferred embodiment, the polyoxypropylene core of the poloxamer/poloxamine has a weight average molecular weight in the range from 2000 to 4000 g/mol, more preferably in the range from 2200 to 3600 g/mol, even more preferably in the range from 2300 to 3300 g/mol.

In a preferred embodiment, the poloxamer/poloxamine has a polyoxyethylene content of from 20 to 70%, more preferably from 30 to 60%, even more preferably from 35 to 55%.

In a preferred embodiment, the poloxamer comprises one or more of poloxamer 234, poloxamer 235, poloxamer 334 and poloxamer 335. Such poloxamers exhibit improved handling properties compared to other poloxamers. It is also preferable that the poloxamine comprises poloxamine 707. Poloxamine 707 has been found to exhibit improved handling properties compared to other poloxamines.

In a preferred embodiment, the resorbable polymer matrix comprises a mixture of: poloxamer 234, poloxamer 235 and polyethylene oxide; or poloxamer 235, poloxamer 334 and polyethylene oxide; or poloxamer 334, poloxamer 335 and polyethylene oxide; or poloxamer 335, poloxamine 707 and polyethylene oxide. These are commercially available polymers.

In a preferred embodiment, the at least one poly(alkylene glycol) polymer and/or at least one methoxypoly(alkylene glycol) polymer has a weight average molecular weight in the range of from 200 to 20,000 g/mol. This results in the biocompatible material exhibiting reduced tackiness. In an alternative embodiment, the at least one poly(alkylene glycol) polymer and/or at least one methoxypoly(alkylene glycol) polymer has a weight average molecular weight of at least 2000 g/mol, at least 3600 g/mol or at least 8000 g/mol. Ensuring weight average molecular weights are within these ranges advantageously results in improvement in the properties of the material such as cohesiveness, adhesiveness and stiffness.

In a preferred embodiment, the at least one poly(alkylene glycol) polymer comprises polyethylene glycol, such as, for example, polyethylene glycol 600. Polyethylene glycol within the resorbable polymer matrix acts like a plasticiser, making the material easier to deform, more kneadable and ductile. In addition, the weight percentage of polyethylene glycol in the resorbable polymer matrix affects the rheology of the material. However, diminishing benefits are exhibited by the material once the amount of at least one poly(alkylene glycol) polymer and/or at least one methoxypoly(alkylene glycol) polymer is increased above 10 wt %.

In a preferred embodiment, the resorbable polymer matrix comprises polyethylene glycol 600, poloxamine and poloxamer 334. In a further preferred embodiment, the polymer matrix comprises from 8 to 12 wt % polyethylene glycol 600, from 8 to 12 wt % poloxamine and from 75 to 85 wt % poloxamer 334. In a still further preferred embodiment, the polymer matrix comprises about 10 wt % polyethylene glycol 600, about 10 wt % poloxamine and about 80 wt % poloxamer 334. Such compositions exhibit improved handling properties.

The at least one additive may be selected from: solid or porous particles (for example calcium phosphate and hydroxyapatite), polymers (for example polyethylene), bioactive compounds (for example biological and pharmaceutical agents), colour pigments and combinations of two or more thereof. Preferred additives include bone chips, bone powder, demineralized bone, calcium phosphate-based compounds, allograft and autograft bone, polyethylene, and any combination of two or more thereof. Calcium phosphate-based compounds include, but are not restricted to, apatite, hydroxyapatite, α- and β-tricalcium phosphate, biphasic calcium phosphate, substituted calcium phosphate, silicate-substituted calcium phosphate, silicate-substituted hydroxyapatite and silicate-substituted tricalcium phosphate. Synthetic silicate-substituted hydroxyapatite is described in U.S. Pat. No. 6,312,468 and is particularly suitable as the at least one additive in the biocompatible material.

In a preferred embodiment, the at least one additive occupies greater than or equal to 10% by volume of said composition, more preferably greater than or equal to 50% by volume of said composition, even more preferably greater than or equal to 92.5% by volume of said composition. A value of greater than or equal to 92.5% enables the composition to provide enough scaffolding materials such that bone in-growth and integration are improved.

In a preferred embodiment, the packing density of the at least one additive in the biocompatible material, i.e. the ratio of the mass of the at least one additive to the volume of the resorbable polymer composition, is from 0.471 to 0.641 g/ml.

In a preferred embodiment, the solid, porous and/or hollow particles have an average diameter from 10 μm to 10 mm, more preferably from 0.09 mm to 10 mm. When the particles have a diameter within the range 0.09 mm to 10 mm, the composition is able to provide enough scaffolding materials for bone in-growth and integration. In an alternative embodiment, the particles can have a diameter in the range from 10 μm to 1000 μm, from 1 mm to 2 mm, or from 2 mm to 10 mm. The ranges are selected for specific applications within the body. For example, materials in the range of from 10 μm to 1000 μm are typically used for filling pedicle screw holes or small defect sites. Materials above this range could be used in spinal applications and hip revision surgery.

In a preferred embodiment, the resorbable polymer matrix exhibits oil- or wax-like handling properties. This improves the ease of handling of the material.

In a preferred embodiment, the resorbable polymer matrix is water-soluble. When the material comes into contact with water, it is advantageous if the resorbable polymer matrix dissolves but the at least one additive does not. This results in the resorbable polymer matrix being readily eliminated from the body in unmodified form. Advantageously, being water-soluble allows the material to pass through the renal system, and not be seen as a foreign body, or interfere with the immune system or the recovery process.

In a preferred embodiment, the materials are mouldable. This means that, in use, the material can be easily shaped to fit the site of administration.

In a second aspect there is provided a biocompatible material for use as a medicament, the biocompatible material being defined according to the first aspect.

In a third aspect there is provided a biocompatible material for use as a replacement bone material or dental implant, the biocompatible material being defined according to the first aspect.

In a fourth aspect there is provided a method of manufacturing the material of the first, second and/or third aspects, the method comprising the steps of:
(1) mixing together the (i) at least one non-random copolymer of poly(alkylene oxide)s with the (ii) at least one poly(alkylene glycol) polymer and/or at least one methoxypoly(alkylene glycol) polymer in dry form without the addition of water or other liquids;
(2) melting at an elevated temperature;
(3) adding the at least one additive; and
(4) aging.

It will be understood that the steps comprising the method of the fourth aspect may be performed either sequentially (1)-(4), or in another suitable order. Alternatively, one or more of the steps may be performed concurrently.

Advantageously, the aging step results in the biocompatible material exhibiting improved handling characteristics.

In a preferred embodiment, the aging is carried out at a temperature of from 20 to 45° C. This provides the material with improved handling characteristics and renders the material in the ideal condition for storage. Preferably, the aging is carried out at a temperature of from 25 to 40° C., more preferably at about 35° C.

In a preferred embodiment, step (1) is carried out under vacuum. This removes any volatiles which may be present in the starting materials.

In a preferred embodiment, the aging is carried out in a relative humidity of from 10 to 90 RH %. This can improve the stability of the material. In a preferred embodiment the relative humidity of the aging step is selected depending on the temperature.

The aging is typically carried out for up to about 48 hours.

In a preferred embodiment, the resorbable polymer matrix is water-soluble. However, the materials are formulated anhydrously, except for minor amounts of absorbed water. The absence of large amounts of water increases the long-term stability of pharmaceutical and/or biological agents, which may be embedded within the resorbable polymer matrix, and consequently the overall product shelf-life.

The method of manufacture according to the fourth aspect typically involves pre-melting the polymers in an oven at an elevated temperature, for example at about 60° C. The materials may then be weighed and dispensed into a commercial vacuum mixer, and processed under temperature control until fully blended. Following mixing, the mixture may be dispensed into moulds and placed into a temperature and humidity controlled oven for up to 48 hours. Following packing, the product may be sterilised by, for example, an electronic beam for medical applications.

In a fifth aspect there is provided a resorbable polymer matrix comprising:
(i) at least one non-random copolymer of poly(alkylene oxide)s; and
(ii) at least one poly(alkylene glycol) polymer and/or at least one methoxypoly(alkylene glycol) polymer.

The resorbable polymer matrix may be used as a bone hemostasis agent.

In a preferred embodiment, the resorbably polymer matrix is biocompatible and non-toxic.

In a sixth aspect there is provided a method of treatment comprising: providing a biocompatible material as herein described in relation to the first aspect; and administering the biocompatible material to a patient.

The material can be provided to the patient in the form of, for example, an adhesive, a cohesive, a filler, a lubricant or a combination of two or more thereof. The method of treatment can include, but is not restricted to, the treatment of bone disorders and/or dental disorders. Examples of bone disorders include, but are not limited to, disorders such as fractures, osteoporosis, osteogenesis imperfecta (brittle bone disease) and joint disorders. Examples of dental disorders include, but are not limited to, tooth chips, tooth cavities and gum disease.

All aspects disclosed in relation to the first aspect may be applied to the second, third, fourth, fifth and/or sixth aspects.

The materials and methods of manufacture will now be described, by way of example only, with reference to the accompanying drawings, in which.

Figure 1:
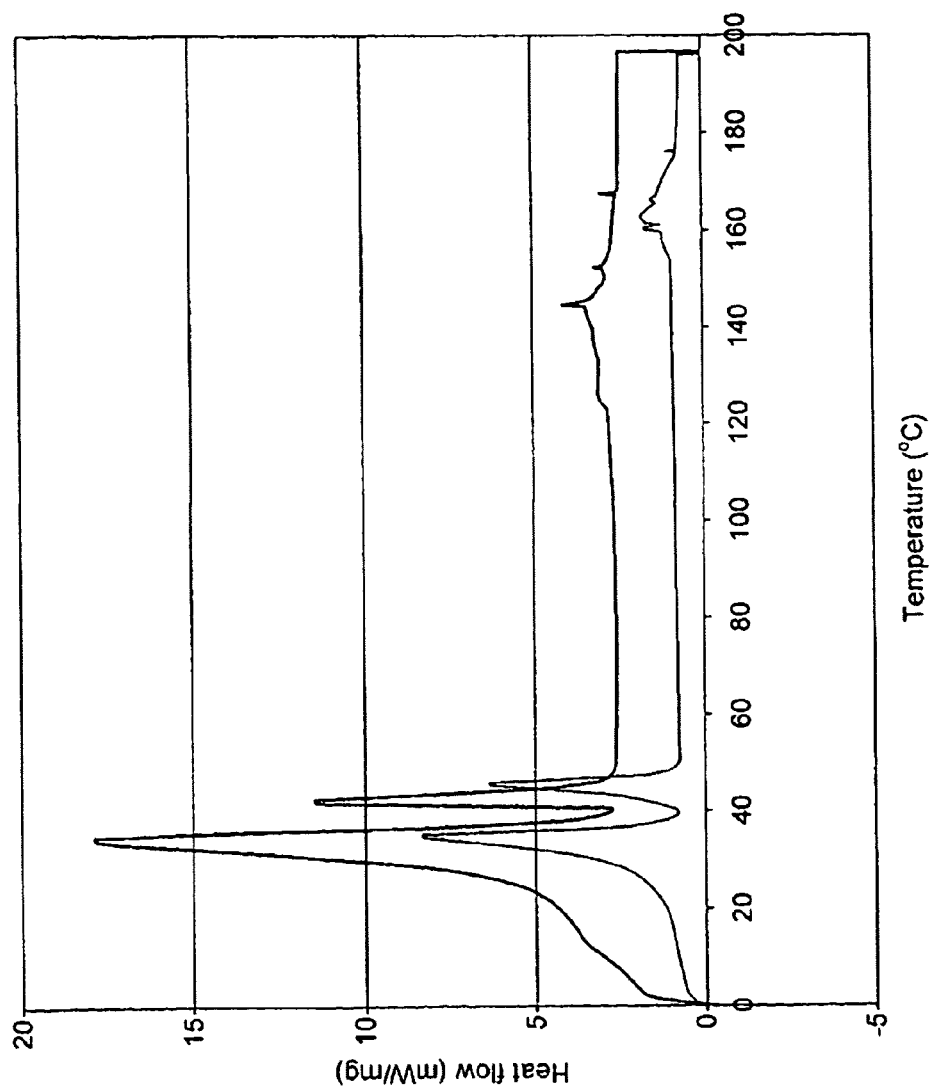
FIG. 1 is a graph of temperature versus heat-flow for a biocompatible material produced according to the method of the fourth aspect described herein.

FIG. 1 shows a graph of temperature versus heat-flow for two biocompatible materials produced according to the method of the fourth aspect described herein. Both materials contain resorbable polymer matrices containing 72.0 wt % of poloxamer 334, 18.0 wt % of poloxamer 335 and 10.0 wt % of polyethylene glycol 600. The plot with the lower baseline heat-flow corresponds to a sample which has undergone an aging step in which the temperature is stable at approximately 35° C. throughout. The sample with the higher baseline heat-flow corresponds to a sample which has undergone an aging step in which the temperature was ramped down from the melting temperature throughout the aging step. Both of the aging steps were carried out for 24 hours. The peak positions indicate the assigned melting temperatures for the resorbable polymer matrix. By varying the heating regime of the aging step, the melting temperature of the resorbable polymer matrix can be modified. This can result in the material being more stable and in a more ideal condition for storage. For example, when comparing the two materials shown in FIG. 1, it can be seen that the material which has been aged at approximately 35° C. exhibits superior handling characteristics under normal surgical conditions. Such handling characteristics include mouldability, cohesiveness and operation window.

Figure 2:
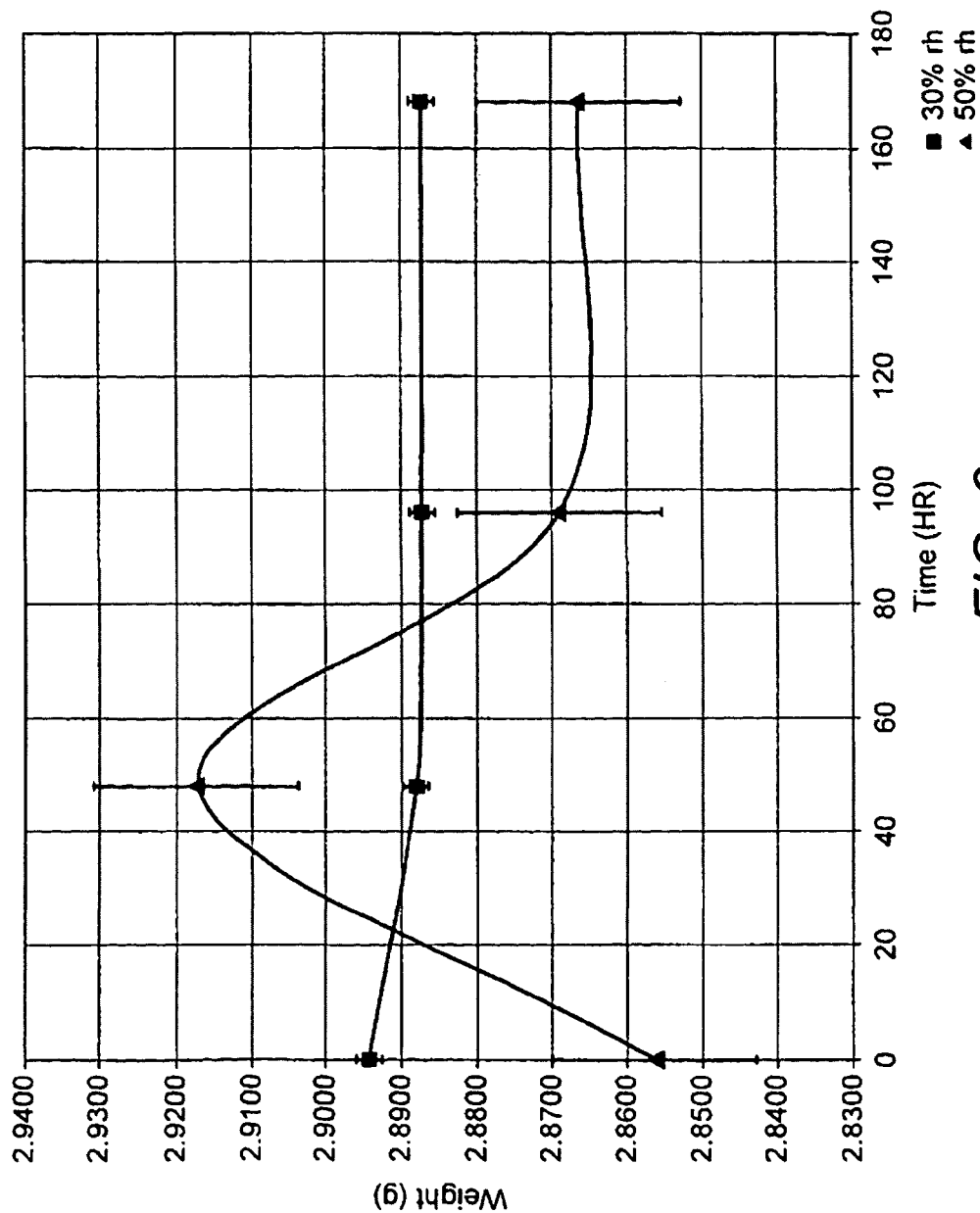
FIG. 2 is a graph of material weight versus aging time for a biocompatible material produced according to the method of the fourth aspect described herein.

FIG. 2 shows a graph of material weight versus aging time for two materials produced according to the fourth aspect described herein. Both materials contain resorbable polymer matrices consisting of 45.0 wt % of poloxamer 334, 45.0 wt % of poloxamer 335 and 10.0 wt % of polyethylene glycol 600. Both materials are aged at 22° C. However, one material is aged in a humidity of 30 RH % and the other in a humidity of 50 RH %. Due to the presence of polyethylene glycol, the time for the materials to reach equilibrium increases with increasing humidity. Accordingly, it is shown that the humidity of the aging step has an effect on the preparation time of the material and/or the material stability.

Figure 3:
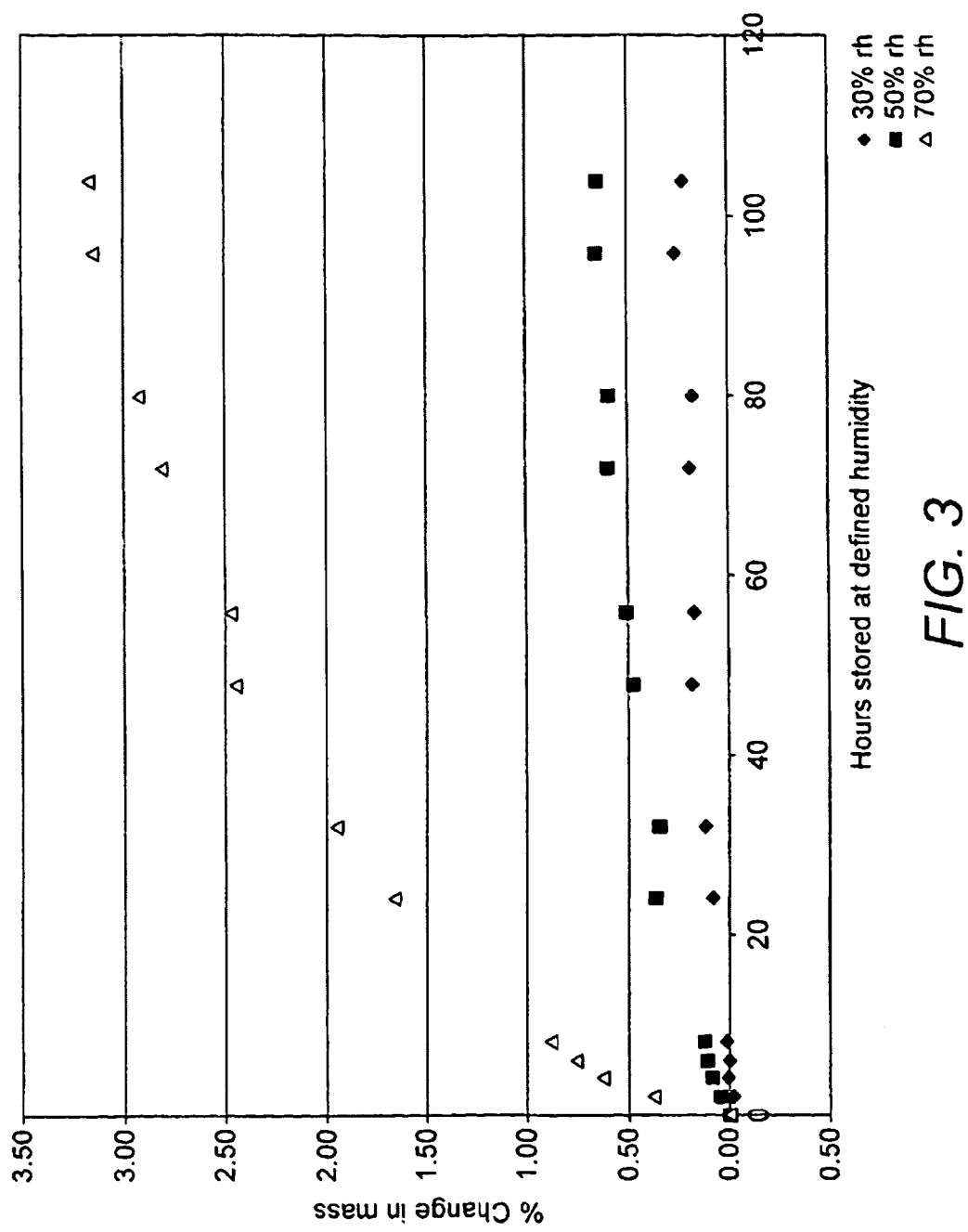
FIG. 3 is a graph of percentage mass change versus storage time under various relative humidity conditions for a biocompatible material produced according to the method of the fourth aspect described herein.

FIG. 3 is a graph of percentage change in mass versus storage time at different relative humidity conditions for a biocompatible material produced according to the method of the fourth aspect described herein. The material contains a resorbable polymer matrix containing 10 wt % polyethylene glycol 600, 10 wt % poloxamine and 80 wt % poloxamer 334. The difference in behaviour when stored under different humidity conditions is a result of the presence of low-molecule polyethylene glycol. This has an impact on the rheology of the polymer mixture, such as cohesiveness and mouldability.

Figure 4:
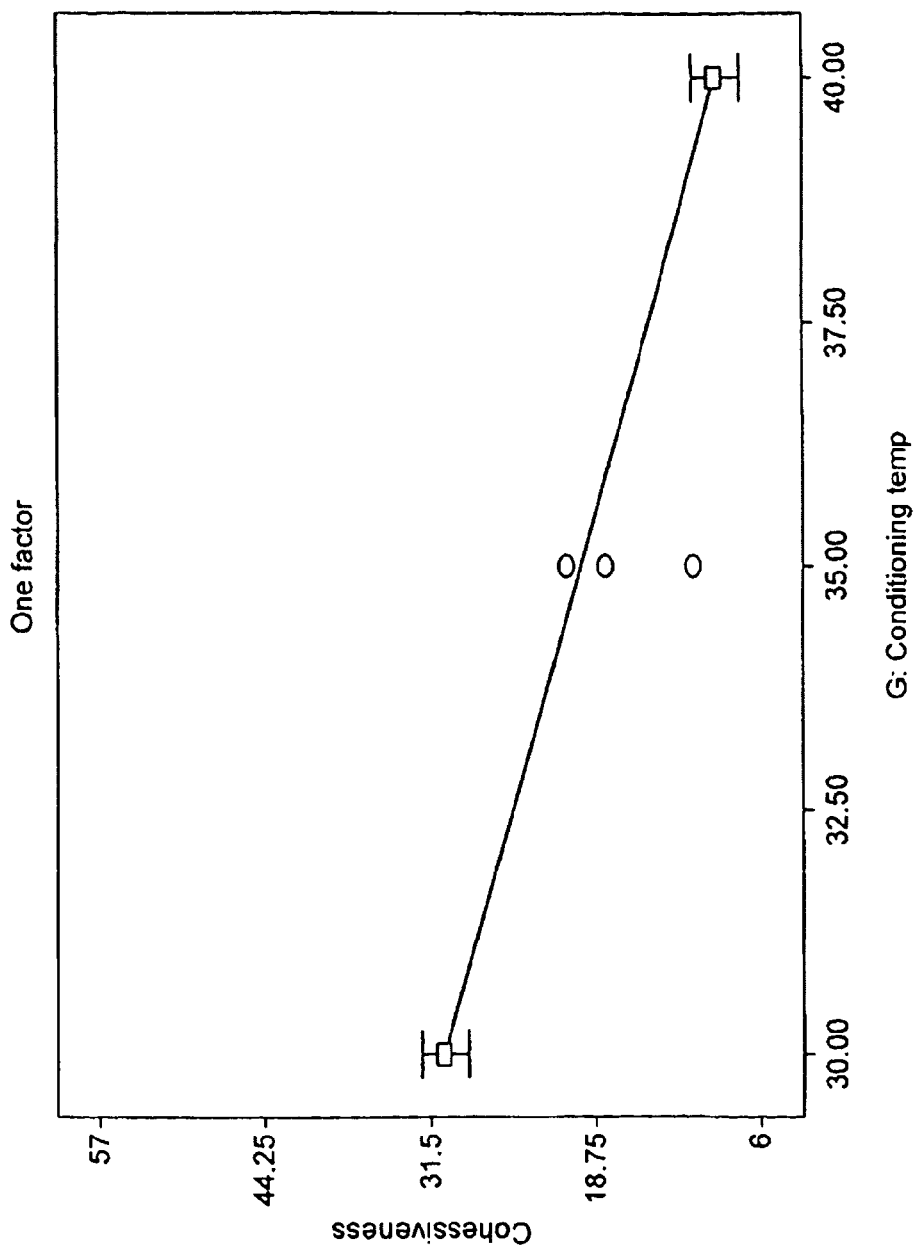
FIG. 4 is a graph of cohesiveness versus conditioning temperature for a biocompatible material produced according to the method of the fourth aspect described herein.
Figure 5:
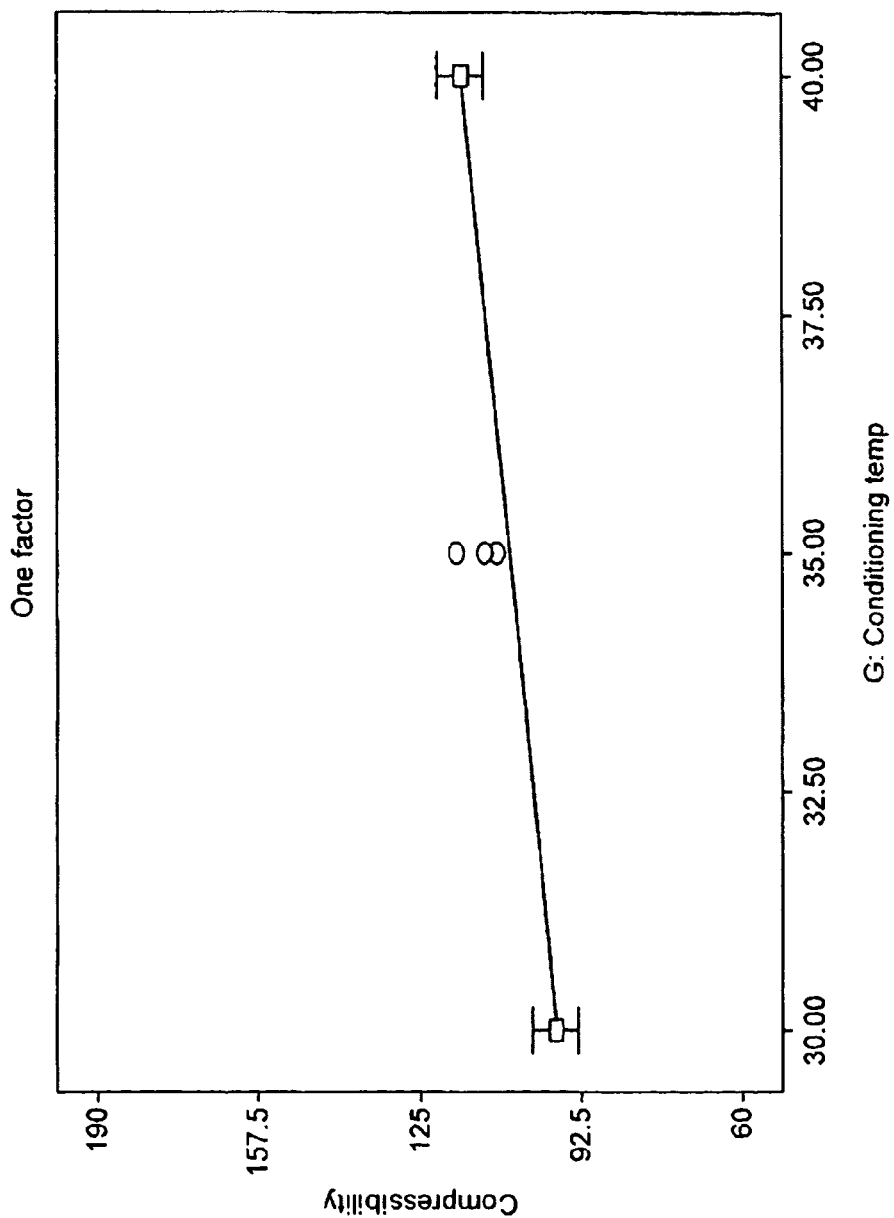
FIG. 5 is a graph of compressibility versus conditioning temperature for a biocompatible material produced according to the method of the fourth aspect described herein.

FIGS. 4 and 5 are graphs of cohesiveness and compressibility respectively versus conditioning temperature for the biocompatible material of FIG. 3.

Figure 6:
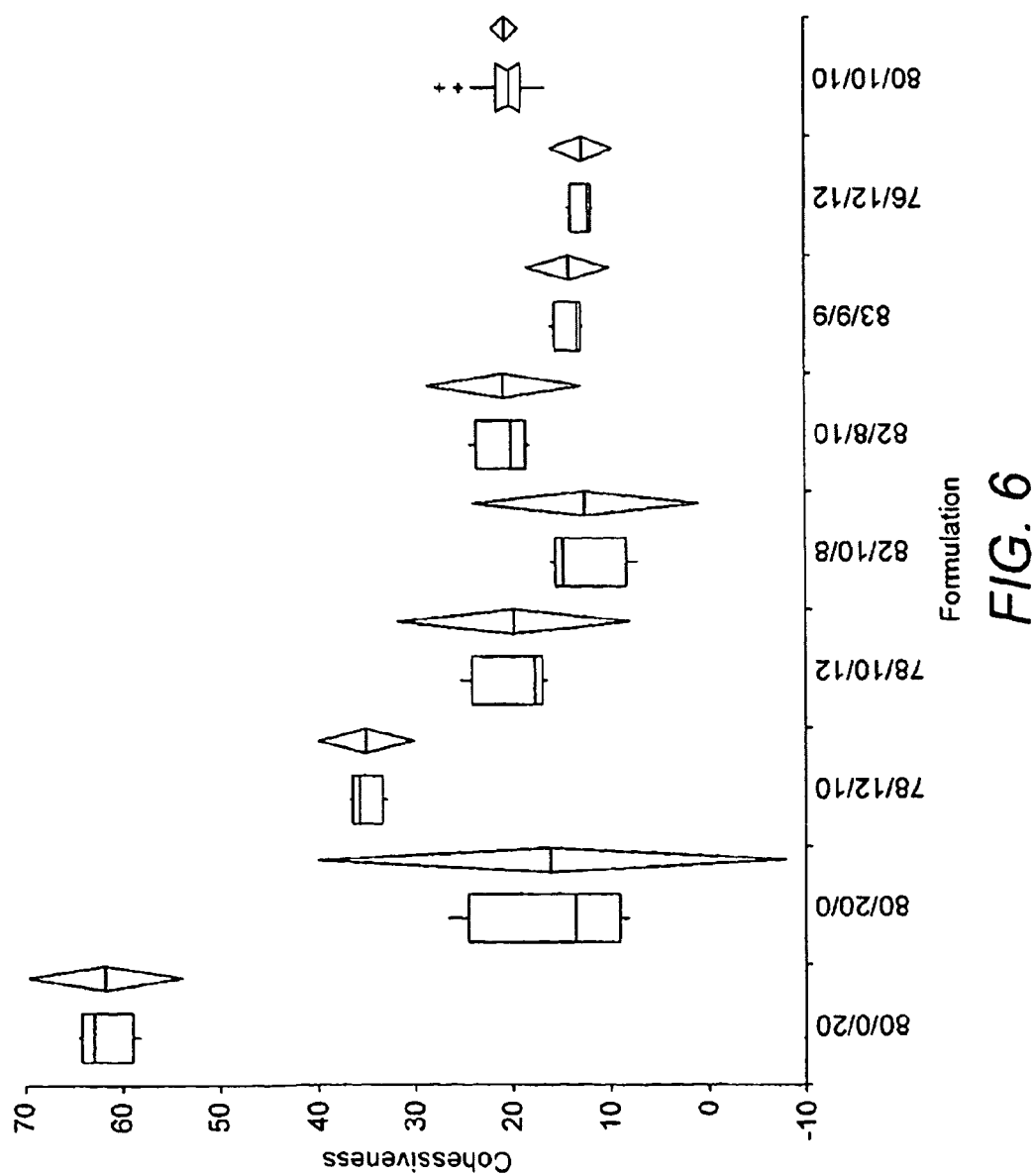
FIG. 6 is a graph of cohesiveness versus composition for a biocompatible material produced according to the method of the fourth aspect described herein.
Figure 7:
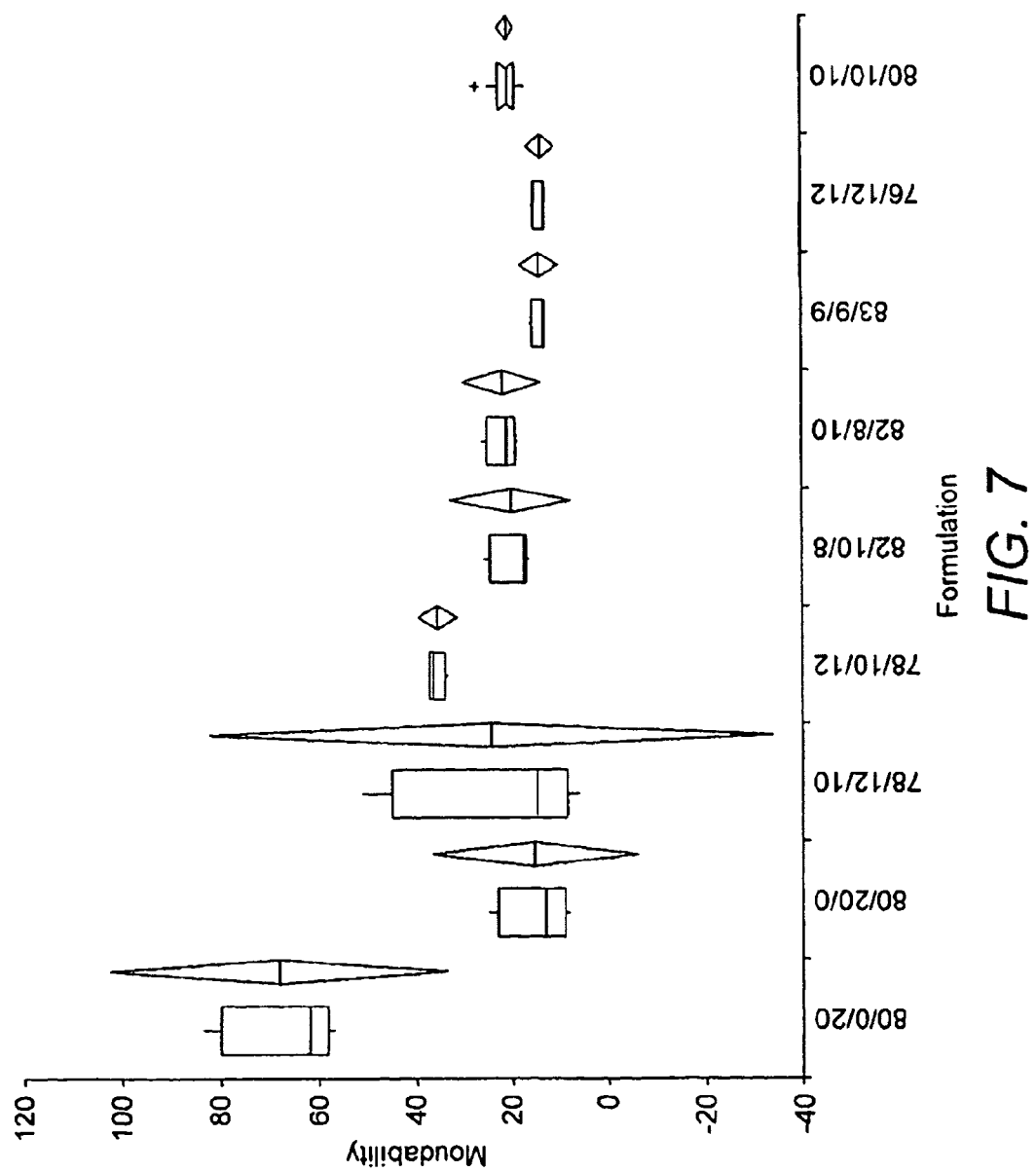
FIG. 7 is a graph of mouldability versus composition for a biocompatible material produced according to the method of the fourth aspect described herein.

FIGS. 6 and 7 are box and whisker plots of cohesiveness and mouldability, respectively, versus composition for a biocompatible material produced according to the method of the fourth aspect described herein. The x axis denotes the wt % of poloxamer 334/poloxamine/polyethylene glycol 600. The centre line of the diamonds indicates the mean values, and the centre line of the boxes denotes the median values. FIGS. 6 and 7 demonstrate the changes in cohesiveness and mouldability respectively with changes in the composition of a tertiary system.

EXAMPLES

The materials and methods of manufacture will now be further described by reference to the following non-limiting examples.

Example 1

Three biocompatible materials were produced comprising silicate-substituted hydroxyapatite as the at least one additive. Such a material is described in U.S. Pat. No. 6,312,468. The resorbable polymer matrices in each material were formed of a poloxomer mixture comprising equal amounts of poloxamers 334 and 335 and varying amounts of polyethylene glycol (PEG) 300. The additive occupied greater than 92.5% by volume of the composition. Deformation tests were carried out on the materials and the results are set out in Table 1:

TABLE 1

Force required to deform material for varying levels of PEG 300
(*sample lost integrity)

| Wt % of Polaxamer 334 | 49 | 45 | 42.5 |
|---|---|---|---|
| Wt % of Polaxamer 335 | 49 | 45 | 42.5 |
| Wt % of PEG 300 | 2 | 10 | 15 |
| Force/N | 64.5 | 43 | 35* |

The results indicate that the use of increased levels of PEG 300 results in the material being easier to deform. However, when the level of PEG 300 is increased beyond 10 wt %, the material becomes too soft and loses its integrity on kneading.

Example 2

Three biocompatible materials were produced comprising silicate-substituted hydroxyapatite as the at least one additive. Such a material is described in U.S. Pat. No. 6,312,468. The resorbable polymer matrix compositions in each material contained varying levels of poloxomer and polyethylene glycol/methoxypolyethylene glycol (MPEG). The additive occupied greater than 92.5% by volume of the composition. The results of deformation tests carried out on these materials are set out in Table 2:

TABLE 2

Force required to deform material for varying compositions and varying aging conditions.

| Resorbable polymer matrix composition: | 30° C., 30 RH % | 35° C., 30 RH % |
|---|---|---|
| 2 wt % PEG600 + 49 wt % poloxamer 334 + 49 wt % poloxamer 335 | 85N | 52.5N |
| 10 wt % PEG600 + 45 wt % poloxamer 334 + 45 wt % poloxamer 335 | 67.5N | 36N |
| 10 wt % MPEG350 + 45 wt % poloxamer 334 + 45 wt % poloxamer 335 | 37N | 28.5N |

The results indicate that the force required to deform the material decreases as the aging temperature increases and/or the wt % of PEG 600 increases. In addition, it can be seen that the use of MPEG 350 results in the material being more deformable when compared to PEG 600.

The foregoing detailed description has been provided by way of explanation and illustration and is not intended to limit the scope of the appended claims. Many variations in the presently preferred embodiments illustrated herein will be apparent to one of ordinary skill in the art, and remain within the scope of the appended claims and their equivalents.

The invention claimed is:

1. A biocompatible material comprising a continuous phase of a resorbable polymer matrix and a non-continuous phase of at least one additive,
   wherein the resorbable polymer matrix comprises:
   (i) a poly(alkylene glycol);
   (ii) a poloxamine; and
   (iii) a poloxamer;
   and wherein the at least one additive is selected from bone chips, bone powder, demineralized bone, calcium phosphate-based compounds, allograft and autograft bone, polyethylene, and combinations of two or more thereof.

2. The material according to claim 1, wherein at least one of the poloxamine and the poloxamer has a weight average molecular weight of less than or equal to 40,000 g/mol.

3. The material according to claim 1, wherein at least one of the poloxamine and the poloxamer has a weight average molecular weight of at least 2000 g/mol.

4. The material according to claim 1, wherein the poloxamine comprises poloxamine 707.

5. The material according to claim 1, wherein the poloxamer comprises one or more of poloxamer 234, poloxamer 235, poloxamer 334, and poloxamer 335.

6. The material according to claim 1, wherein the at least one of the poloxamine, the poloxamer and the poly(alkylene glycol) has a weight average molecular weight in the range of from 200 to 20,000 g/mol.

7. The material according to claim 1, wherein the poly(alkylene glycol) comprises polyethylene glycol.

8. The material according to claim 7, wherein the polyethylene glycol is polyethylene glycol 600.

9. A biocompatible material comprising a resorbable polymer matrix and at least one additive, wherein the resorbable polymer matrix comprises from 8 to 12 wt % polyethylene glycol 600, from 8 to 12 wt % poloxamine and from 75 to 85 wt % poloxamer 334, and wherein the at least one additive is selected from solid particles, porous particles, hollow particles, polymers, inert fillers, bioactive compounds, colour pigments and combinations of two or more thereof.

10. The material according to claim 1, wherein the at least one additive occupies greater than or equal to 10% by volume of said composition.

11. The material according to claim 9, wherein the solid or porous particles have an average diameter of from 10 microns to 10 mm.

12. The material according to claim 1, wherein the resorbable polymer matrix is water soluble.

13. The material according to claim 1, wherein the material is mouldable.

14. A resorbable polymer matrix comprising:
   (i) at least one of: poloxamer 234, poloxamer 235, poloxamer 334, poloxamer 335;
   (ii) a poloxamine; and
   (iii) at least one methoxypoly(alkylene glycol) polymer.

15. The material according to claim 1, wherein the resorbable polymer matrix comprises:
   the poly(alkylene glycol) in an amount ranging from 8 to 12 wt % wherein the poly(alkylene glycol) comprises polyethylene glycol 600,
   the poloxamine in an amount ranging from 8 to 12 wt %, and
   the poloxamer in an amount ranging from 75 to 85 wt %, wherein the poloxamer comprises poloxamer 334.

* * * * *